United States Patent [19]
Samour et al.

[11] Patent Number: 5,942,545
[45] Date of Patent: Aug. 24, 1999

[54] COMPOSITION AND METHOD FOR TREATING PENILE ERECTILE DYSFUNCTION

[75] Inventors: Carlos M. Samour, Bedford; Scott F. Krauser, Tyngsboro, both of Mass.; Robert J. Gyurik, Exeter, N.H.

[73] Assignee: MacroChem Corporation, Lexington, Mass.

[21] Appl. No.: 08/864,130

[22] Filed: May 27, 1997

[51] Int. Cl.⁶ ..................... A61K 31/557; A61K 31/495; A61K 31/50; A61K 31/415
[52] U.S. Cl. .......................... 514/573; 514/254; 514/401
[58] Field of Search .................................. 514/573, 254, 514/401

[56] References Cited

U.S. PATENT DOCUMENTS

| | | |
|---|---|---|
| 4,127,118 | 11/1978 | Latorre . |
| 4,311,707 | 1/1982 | Birnbaum et al. . |
| 4,801,587 | 1/1989 | Voss et al. . |
| 4,861,764 | 8/1989 | Samour et al. . |
| 5,059,603 | 10/1991 | Rubin . |
| 5,145,852 | 9/1992 | Virag . |
| 5,219,885 | 6/1993 | Frolich et al. . |
| 5,236,904 | 8/1993 | Gerstenberg et al. . |
| 5,242,391 | 9/1993 | Place et al. . |
| 5,256,652 | 10/1993 | El-Rashidy . |
| 5,270,323 | 12/1993 | Milne, Jr. et al. . |
| 5,336,678 | 8/1994 | Cavallini . |
| 5,380,760 | 1/1995 | Wendel et al. . |
| 5,399,581 | 3/1995 | Laragh . |
| 5,439,938 | 8/1995 | Snyder et al. . |
| 5,447,920 | 9/1995 | Matsuda et al. . |
| 5,451,609 | 9/1995 | Bellamy et al. . |
| 5,464,868 | 11/1995 | Frolich et al. . |
| 5,475,535 | 12/1995 | Eckhardt . |
| 5,482,039 | 1/1996 | Place . |
| 5,488,059 | 1/1996 | Buhl . |
| 5,492,911 | 2/1996 | Stief . |
| 5,527,797 | 6/1996 | Eisenberg et al. . |
| 5,565,466 | 10/1996 | Gioco et al. . |
| 5,583,144 | 12/1996 | Kral et al. . |
| 5,587,167 | 12/1996 | Choi et al. . |
| 5,594,032 | 1/1997 | Gonzalez-Cadavid . |
| 5,620,980 | 4/1997 | Samour . |

FOREIGN PATENT DOCUMENTS

| | | |
|---|---|---|
| 277720 | 1/1993 | Czechoslovakia . |

OTHER PUBLICATIONS

Williams, et al., Skin Absorption Enhancers, Crit. Rev. Ther Drug Carrier Syst 1992(3–4) Abstract.
Monkhouse, et al., J. of Pharm. Sciences, vol. 62, No. 4, Apr. 1973.
Teagarden, et al., Dehydration Kinetics of Prostaglandin $E_1$ in a Lipid Emulsion, Pharmaceutical Research, vol. 6, No. 3, 1989.
Stehle, et al., Journal of Pharmaceutical Sciences, vol. 66, No. 11, Nov. 1977.
Anderson, et al., Prodrugs and Their Topical Use, Topical Drug Bioavalability, Bioequivalence, and Penetration, Plenum Press, 1993.
Montorsi, et al., Pharmacological Management of Erectile Dysfunction, Drugs 50(3), 1995, pp. 465–479.
Fuhrman, et al., Pred. of Percutaneous Penetration, vol. 4B, 1996.
American Society of Andrology, 1995 Annual Meeting, Mar. 31–Apr. 4, 1995, Abstract re Induction of Erections in Anesthetized Cynomologus Monkeys.
American Society of Andrology, 1994 Annual Meeting, Mar. 4–7, 1994, Abstract re Treatment of Erectile Dysfunction in Men with Diabetes Mellitus.
Watkinson, et al., Aspects of the transdermal delivery of prostaglandins, Int. J. of Pharma. 74(1991) 229–236.
Kim and McVary, Topical prostaglandin–E1 for the treatment of erectile dysfunction, Journal of Urology, vol. 158, 1828–1830 (1995).
Kim, et al., Papaverine topical gel for treatment of erectile dysfunction, Journal of Urology, vol. 158, 361–385 (1995).
Gomaa, et al., Topical treatment of erectile dysfunction: randomised double blind . . . , British Med. Journal, 312:1512–1515 (1995).
Becher, et al., Abstract, A Double bind placebo controlled trial of topical prostaglandin E1 . . . , San Francisco, CA symposium (1997).
Linet, et al., Efficacy and safety of intracavernosal alprostadil in men with erectile dysfunction, New England J. of Medicine, 334(14):873–877, 1996.
Padma–Nathan, et al., Treatment of men with erectile dysfunction with transurethral alprostadil, New England J. of Medicine, 336(1):1–7, 1997.
Anderson, et al., Topical nitrate treatment of impotence, Annals of Pharmacotherapy, 27:1203–1205 (1993).
MacroChem Press Release, Mar. 5, 1996, "MacroChem Announces Initiation Of A Phase I/II Clinical Trial of a Topical Gel Containing Prostaglandin E1 . . . ".
MacroChem Press Release, May 14, 1996, "MacroChem Initiates Phase I/II Clinical Trial of Topical Formulation For Erectile Dysfunction".
MacroChem Press Release, Dec. 10, 1996, "MacroChem Announces Positive Results Attained in a Phase I/II Clinical Trial of Topical Gel For Erectile Dysfunction".

*Primary Examiner*—William R. A. Jarvis
*Attorney, Agent, or Firm*—Sherman and Shalloway

[57] ABSTRACT

A composition for the topical transdermal administration to the penis is based on prostaglandin $E_1$. The composition is non-irritating and effective for relieving erectile impotence or other penile erectile dysfunction. A penetration enhancing effective amount of a dioxolane, dioxane, or acetal skin penetration enhancing compound in a pharmaceutically acceptable aqueous alcoholic carrier is used to facilitate the penetration of the prostaglandin $E_1$ active ingredient through the skin. Phentolamine or prazosin may be used in combination with prostaglandin $E_1$.

23 Claims, No Drawings

COMPOSITION AND METHOD FOR TREATING PENILE ERECTILE DYSFUNCTION

BACKGROUND OF INVENTION

1. Field of Invention

The present invention relates to compositions and methods for treating penile erectile dysfunctions, such as male erectile impotence, and more particularly, to compositions and methods for the topical administration to the penis effective for the treatment of penile erectile dysfunctions.

2. Background of the Invention

Impotence is generally characterized as the inability to develop or sustain an erection sufficient to conclude coitus. Many men are afflicted with a degree of impotence resulting from psychological and physiological conditions. Causes of impotence are numerous. These include atonic, due to paralysis of the motor nerves (nervi erigentes) without any evidence of lesion to the central nervous system. Conversely, it could be paretic as a result of a lesion in the central nervous system, particularly the spinal cord. Alternatively, it could be psychic, and dependent on a mental complex or instability. The cause may also be symptomatic, due to some other disorder, such as injury to nerves in the perineal region, by virtue of which the sensory portion of their erection reflex is blocked out. (See, e.g., U.S. Pat. No. 4,801,587.)

Specific physiological disorders which may be the cause of penile erectile dysfunction or male impotence, and for which the present invention may be used, in addition to psychological causes, include, for example, pelvic vascular disease, diabetes mellitus, neurodegenerative disorders, side effects of medication, pelvic surgery, trauma, and the like.

One widely used solution for treating impotency involves implants which, in essence, are internal prostheses. However, implants, which often include surgery, are expensive and not always effective.

The other major solution for treating male impotence is via use of drugs. Since erection necessarily involves vasodilation of the arteries of the penis, the pathophysiologic basis of impotence can often be treated by vasodilation agents. There have been and are ongoing clinical and experimental research efforts to develop new and better drugs and delivery routes for such drugs. These efforts have been the subject of several literature articles and issued patents including, for example, the following United States Patents: U.S. Pat. No. 4,801,587—Voss, et al; U.S. Pat. No. 5,256,652—El-Rashidy; U.S. Pat. No. 5,336,678—Cavallini; U.S. Pat. No. 5,583,144—Kral; U.S. Pat. No. 5,475,535—Place, et al; U.S. Pat. No. 5,482,039—Place; U.S. Pat. No. 5,451,609—Bellamy, et al; U.S. Pat. No. 5,242,391—Place, et al; U.S. Pat. No. 5,145,852—Virag; U.S. Pat. No. 5,399,581—Laragh; U.S. Pat. No. 5,270,323—Milne, et al; U.S. Pat. No. 5,236,904—Gerstenberg, et al; U.S. Pat. No. 4,127,118—Latorre; U.S. Pat. No. 5,565,466—Gioco, et al; U.S. Pat. No. 5,492,911—Stief; U.S. Pat. No. 5,594,032—Gonzalez-Cadavid, et al; U.S. Pat. No. 5,488,059—Buhl; U.S. Pat. No. 5,439,938—Snyder, et al.

While the interested reader should refer directly to the above patents and the patents and literature discussed or cited in these patents, as well as the literature discussed below, the following brief discussion is provided.

U.S. Pat. No. 5,583,144 is based on the use of piperoxan for treatment of erectile impotence and includes a disclosure of topical administration. The combination of piperoxan with prostaglandins, particularly PGE2, is disclosed. The compositions for topical administration include gels, (including hydrogels), ointments, creams, etc. but without any details.

Generally, however, the patent art reveals that topical or transdermal application of the treating agent is not available or preferred: U.S. Pat. No. 5,451,609 (injection per intracavernosal route); U.S. Pat. No. 5,242,391 (urethral insert); U.S. Pat. No. 5,145,582 (PGE1 with papaverine); U.S. Pat. No. 5,399,581 (enteral); U.S. Pat. Nos. 5,270,323; 5,236,904 (intracavernosal injection); and U.S. Pat. No. 4,127,118 (injection).

Patents which disclose topical (transdermal) formulations include U.S. Pat. No. 5,256,652 ('652) and U.S. Pat. No. 5,336,678 ('678). The '678 patent is directed to the topical administration of from 0.1 to 10% minoxidil. Patentees divide the drugs for treating erectile impotence into three class:

1) oral, e.g., yohimbine;

2) intracavernous injection, e.g., PGE1;

3) topical, e.g., nitroglycerin.

The '652 patent describes a topical composition which includes an absorption enhancer and, optionally, a vasoconstrictor and an alpha receptor blocker. The enhancer is a cyclodextrin, particularly, hydroxypropyl-beta-cyclodextrin (HPBCD).

The '652 patent refers to U.S. Pat. No. 4,311,707 ('707) as disclosing topical administration of prostaglandins including an alleged use to treat impotency. U.S. Pat. No. 4,801,857 ('857) is also discussed in the '652 patent. This patent discloses a topical ointment for treating impotence.

Other references which may be of interest include: U.S. Pat. No. 5,587,167 (topical composition with extract of ginseng radix for prophylaxis and treatment of premature ejaculation); U.S. Pat. No. 5,565,466 (modulating the human sexual response by oral mucosal, intranasal or rectal administration of vasodilator); U.S. Pat. No. 5,492,911 (Linsidomine, alone or in combination with, prostaglandins, for injection); U.S. Pat. No. 5,447,920 (cosmetic composition, inclusion product of HPBCD); U.S. Pat. No. 5,594,032 (inducible Nitric Oxide Synthase (NOS) agents; non-topical modes); U.S. Pat. No. 5,488,059 (pyridylguanidine compound by injection into corpus cavernosum or transdermal); and U.S. Pat. No. 5,439,938 (inhibitors for NOS, topical application).

Transdermal delivery of prostaglandins has been the subject of scientific study. In a report titled "Aspects of the transdermal delivery of prostaglandins" by A. C. Watkinson, et al, International J. of Pharmaceutics, 74:229–236, 1991, the authors studied in vitro skin penetration through human skin for prostaglandins $E_1$, $E_2$, $F_{1\alpha}$, and $F_{2\alpha}$ and the influence of absorption rates using the enhancers Azone® and Transcutol (2-ethoxy-ethoxy ethanol). Preapplication of the enhancer to the skin was found to facilitate drug flux. However, the enhancement for PGE-1 was not as significant as for PGE-2. The greatest enhancement was found after pretreatment with a mixture of Azone and Transcutol, approximately 10% after 48 hours.

Although topical nitroglycerin, minoxidil, papaverine and prostaglandin $E_1$ (PGE-1) have been studied, their efficacy, as documented in the scientific literature, has been wanting. Anderson, et al, "Topical Nitrate Treatment of Impotence", Ann. Pharmacotherapy, 27:1203–1205, 1993, provide a review of the earlier literature and their conclusion is that there is insufficient evidence that topical application is efficacious. Kim and McVary, "Topical Prostaglandin-E1 for the Treatment of Erectile Dysfunction", J. Urol 158:1828–1830, 1995a, reported only 20% (2 of 10) of patients treated with a topical gel containing 0.4% PGE-1 had erections with intermediate rigidity. The carrier of the topical gel is not described. The authors concluded that the PGE-1 gel resulted in a significant increase in cavernous artery diameter and peak systolic flow velocity and appeared to be well tolerated after genitalia and forearm application. However, the results of topical absorption were not conclusive. It is further stated that, "Prostaglandin-E1 gel may have promise at higher concentrations, with different skin enhancers or in combination with other topical agents." Further investigation was deemed warranted.

In another study, significant increases in erectile response were seen after topical application of 0.5% PGE-1 and 67% of the patients achieved rigidity consistent with penetration. However, the erections did not persist after the end of stimulation (Montorsi, et al, Drugs 50(3):465–479, 1995a; Intern. J. Impotence Res. 7:10, 1995b). In neither of these reports were there noted any adverse events attributable to the application of PGE-1. It was suggested that an increased penetration of the active agent through the skin and/or into the erectile tissues may be required to have an improved response.

In the case of papaverine, topical application to the penis of 133 to 500 milligrams (mg) of an aqueous gel containing papaverine hydrochloride in concentrations of 7, 15 or 20% was studied (Kim, et al, J. Urol 158:361–365, 1995b). The 15% and 20% formulations elevated cavernosal arterial diameter (by about 36%) and peak systolic blood flow (by about 26%) in patients with spinal injury. However, while three of the seventeen patients treated had tumescence and erections, they also likewise responded following application of a placebo gel. Nevertheless, erections after the papaverine gel lasted longer, although this result was not statistically significant.

Gomaa, et al. (British Med. Journal 312:1512–5, 1995) reports that a topical formula ("cream") containing three actives (3% aminophylline, 0.25% isosorbide dinitrate and 0.05% co-dergocrine mesylate) is effective in the treatment of erectile dysfunction.

Becher, et al, in an Abstract ("A Double Blinded Placebo Controlled Trial of Topical Prostaglandin E1 for Erectile Dysfunction") presented at the Erectile Dysfunction Symposium held in San Francisco, Calif., in February 1997, reported that in three pilot studies using three different formulations on 51 impotent patients 33% (5 of 15) responded to a formulation with 2 mg PGE-1, as compared to 13% responding to the placebo; 61% (11 of 18) responded to a formulation with 4 mg PGE-1, as compared to 39% responding to placebo; and 66% (12 of 18) responded to a formulation containing 4 mg PGE-1 and nitroglycerin, as compared to 39% responding to placebo. In these studies, one patient developed a skin rash and one had an episode of hypotension. The compositions used in the trials are not described.

Linet, et al, The New England J. of Medicine, 334(14):873–877 (Apr. 4, 1996) describes a study on the efficacy and safety of alprostadil administered by intracavernosal injection for treatment of erectile dysfunction in men. Among other side effects 54 of the 235 men (23 percent) experienced penile pain. Alprostadil is a synthetic prostaglandin $E_1$. In an accompanying editorial (L. Lipshultz, pages 913–14) the Linet study was described as the "largest prospective, multi-institutional study thus far undertaken of the injection of a single drug. (footnote omitted.) The authors not unexpectedly found that alprostadil produced significantly better erections than placebo and that the response was dose-dependent." The editorial goes on to explain that of the 577 men studied, 69 percent completed the six-month study; 87 percent reported that the injections resulted in satisfactory sexual activity. Of the 31 percent that did not complete the study lack of efficiency was a prominent complaint. 683 men were evaluated for side effects and 50 percent reported penile pain. In a different study using alprostadil 17 percent discontinued therapy because of severe pain with an additional 22 percent having mild-to-moderate pain. Dr. Lipshultz concludes that intracavernous injections are a well-accepted and efficacious treatment for erectile dysfunction whereas, "[o]ther ways of administering alprostadil, such as by a medicated urethral system (footnote omitted) and in a topical gel,[10] have not yet been demonstrated to have similar results." Footnote 10 was to the above article by Kim and Mcvary (1995a).

In an even more recent study of treatment of erectile dysfunction with alprostadil, Padma-Nathan, et al, The New England J. of Medicine, 336(1):1–7, Jan. 2, 1997, a transurethral delivery mechanism was used. Nearly 88% of the 996 men in the study completed the entire three-month treatment period. The transurethral administration of alprostadil was found to be effective in 69% of the men in the alprostadil group. However, penile pain (categorized as mild) was reported by almost 36% of the men during the clinical testing while over 2% discontinued the study because of the pain. In the home treatment phase penile pain was reported after 10.8% of the alprostadil administrations and by nearly 33% of the men. These authors refer, at page 6, to alternative methods of delivery, including an intraurethral cream containing prostaglandin $E_2$ applied to the urethral meatus. Of the 20 men in this study full penile tumescence was reported to have occurred in 30 percent of the subjects. The authors also refer to the Kim and McVary pilot study of transdermal PGE-1 as failing to induce rigid erections, apparently because of insufficient transfer of the drug through skin.

It is known from U.S. Pat. No. 4,861,764 to Carlos M. Samour and Stefanous Daskalakis (and commonly assigned with the subject application) that 1,3-dioxolanes and 1,3-dioxanes, including, for example, 2-n-pentyl-, 2-n-heptyl-, 2-n-nonyl-, 2-n-undecyl-, pentylene-1,5-bis- 1,3-dioxolanes; 2-n-nonyl-, 2-n-undecyl-, 2-(2',6'-dimethyl-2'-heptadienyl)- 1,3-dioxanes; are useful as percutaneous absorption enhancers for enhancing skin penetration of therapeutic agents.

As described more recently in the partially commonly assigned U.S. Pat. No. 5,527,797 to Eisenberg and Samour, the above 1,3-dioxanes, 1,3-dioxolanes and other alkyl or alkenyl substituted compounds of general formula R–X (where R is a $C_5$ to $C_{28}$ alkyl or alkenyl; X is 1,3-dioxane; 1,3-dioxolane; 5-, 6-, 7-, or 8-numbered lactam; cycloalkylene carbonate, —COOH, —OH, cycloalkylene carbonate; —COOR' (R' is a lower alkyl or unsaturated lower alkyl); —(OCH$_2$CH$_2$)$_n$—OH (n is an integer of from 1 to about 20); —OC(O)R'; R'OC(O)—; —C(O)N(R')$_2$; acetals; and hemiacetals; can be used as water-insoluble or substantially water-insoluble stratum corneum-lipid modifiers for enhancing transportation of charged molecules through skin by iontophoresis.

Recently issued U.S. Pat. No. 5,620,980 to C. Samour, also commonly assigned with this application, discloses the use of the 1,3-dioxolanes and 1,3-dioxanes in a topical formulation containing minoxidil for treating hair loss.

There is no suggestion in the prior art, as described above, which would have led the practitioner to understand or believe that the 1,3-dioxolanes and 1,3-dioxanes or acetals would have been effective for enhancing penetration of prostaglandins, especially, prostaglandin $E_1$ (PGE-1), or any other vasodilating agent or other drug effective for use in the treatment of erectile dysfunction. In fact, the use of these skin penetration enhancing compounds in combination with PGE-1, phentolamine, prazosin, etc., can be considered to be contra-indicated by the prior art.

For example, though the dioxanes and dioxolanes are known as penetration enhancers, delivery of elevated drug levels via a non-vascular route directly into target sites deep below the skin was not to be expected. The well-vascularized dermis would be expected to rapidly remove a drug before it can penetrate into the deeper target tissues, in this case, the corpora cavernosa and spongiosum. Furthermore, the cavernosa are covered by a thick tissue, the tunica albuginea, whose barrier properties are very different from that of the skin.

Secondly, the major barrier function of the skin, the stratum corneum, is virtually absent on the glans of the penis, which is the site of most likely maximum absorption because of its communication with the above mentioned corpora. Since the 1,3-dioxanes, 1,3-dioxolanes and acetals are well known as skin penetration enhancers whose mechanism of action is the temporary disruption of the stratum corneum, its enhancement of permeation of therapeutically active amounts of drug through this non-cornified organ structure would not have been expected.

Although not specifically addressed in the above mentioned prior art relating to topical formulations for treating erectile dysfunction, PGE-1 is substantially insoluble in water. Attempts to increase solubility by increasing the pH of the system are of limited use since the stability of PGE-1 decreases at pH levels above the pKa of the free acid.

Accordingly, it is an object of the invention to provide a prostaglandin composition effective for topical delivery in the treatment of penile erectile dysfunction.

It is a related object to provide a topical formulation for transdermal delivery which is more effective than known formulations and easier to use than injectable formulations or implants.

Still another object of the invention is to provide a topical composition for transdermal delivery of active agent for treatment of penile erectile dysfunction wherein the composition may be applied to only the glans of the penis.

SUMMARY OF INVENTION

The above and other objects of the invention, which will become more apparent in connection with the following detailed description, are achieved by a composition for the topical transdermal administration to the penis of a patient in need thereof, the composition comprising (a) a pharmacologically effective amount of prostaglandin $E_1$;

(b) an effective amount of a skin penetration enhancing compound selected from the group consisting of $C_6$ to $C_{20}$-hydrocarbyl group substituted 1,3-dioxane, 1,3-dioxolane and acetal;

(c) a pharmaceutically effective carrier comprising
 (i) a mixture of ethyl alcohol and water effective to solubilize the components (a) and (b);
 (ii) a mixture of isopropyl alcohol and water effective to solubilize the components (a) and (b); or
 (ii) a mixture of propylene glycol with either ethanol or isopropyl alcohol or both of these alcohols; and (d) a gelling effective amount of a gelling agent; and, optionally, (e) an anti-irritating effective amount of menthol.

In another aspect, the invention provides a method for treating penile erectile dysfunction in a patient in need thereof comprising topically administering to the genitalia of the patient a composition comprising a pharmacologically effective amount of prostaglandin $E_1$ in the presence of a skin penetration enhancing effective amount of a skin penetration enhancing compound selected from the group consisting of $C_6$ to $C_{20}$-hydrocarbyl group substituted 1,3-dioxolane, 1,3-dioxane and acetal; wherein the prostaglandin $E_1$ and the skin penetration enhancing compound are solubilized in a pharmacologically acceptable aqueous-alcoholic carrier comprising ethyl alcohol and water, isopropyl alcohol and water; or a non-aqueous carrier comprising ethyl alcohol and/or isopropyl alcohol, and propylene glycol; and a thickening agent in an amount effective to retain the prostaglandin $E_1$ and skin penetration enhancing compound on the penis.

According to an embodiment of the invention process, the topical composition is applied topically to only the glans penis.

DETAILED DESCRIPTION AND PREFERRED EMBODIMENTS

The compositions and method of this invention can be used for the treatment of any of the underlying causes of penile erectile dysfunction or male impotence, including for example, pelvic vascular disease, diabetes mellitus, neuro-degenerative disorders, pelvic surgery, side effects of other medications, trauma and psychological problems.

The compositions of the invention are intended for topical, non-invasive, application to the genital regions, especially the penis, its entirety, or preferably just the glans of the penis. In addition, the composition may be applied to the scrotum and/or perineum. One particular advantage of this invention is that the composition is effective even when applied to only the glans penis; another advantage is the reduction of side effects, such as burning sensation or pain.

The term "non-invasive" means the treatment does not require puncturing the skin, surgical removal of tissue, or any other kind of surgical intervention, including transurethral administration.

The active ingredient in the formulations of this invention is prostaglandin $E_1$ (PGE-1) [11,15-dihydroxy-9-oxoprost-13-en-1-oic acid; 3-hydroxy-2-(3-hydroxy-1-octenyl)-5-oxo-cyclopentaneheptanoic acid] which is a known vasodilator. However, other prostaglandins, such as prostaglandin $E_2$ (PGE-2), or prostaglandin-mimetics, or other drugs useful for treatment of penile erectile dysfunctions, such as, for example, papaverine (1-[3,4-dimethoxyphenyl)methyl]-6,7-dimethoxyisoquinoline), dioxyline, ethaverine (1-[(3,4-diethoxyphenyl)methyl]-6,7-diethoxyisoquinoline), phentolamine (3-[[4,5-dihydro-1H-imidazol-2-yl)methyl](4-methylphenyl)amino]phenol), prazosin (1-(4-amino-6,7-dimethoxy-2-quinazolinyl)-4-(2-furanylcarbonyl) piperazine), minoxidil, nitroglycerin, alpha blockers, nitric oxide donors, peptides (e.g., VIP), may also be used. Especially, mixtures of PGE-1 with phentolamine or prazosin are preferred; for example at ratios of PGE-1 to phentolamine or prazosin of from 1:200 to 1:1, preferably 1:100 to 1:5, more preferably 1:50 to 1:10.

Generally, the amount of active ingredient to be applied will depend on such factors as the particular disorder being treated, severity of the disorder, the age of the patient, the amount and type of enhancer. Usually, amounts ranging from about 25 μg to about 4 mg of PGE-1 per application, preferably from about 50 μg to about 2.5 mg of PGE-1, more preferably from about 125 μg to about 1.5 mg, per application, will provide acceptable results for most individuals. Accordingly, PGE-1 will usually be included in the compositions for topical application in amounts ranging from about 0.001 to 5.0 percent (as used herein, unless otherwise noted, all percents, percentages, amounts, and ratios, are on a weight basis), preferably 0.05 to 1.5 percent, more preferably from about 0.05 to 1.0 percent, based on the total composition. Where PGE-1 is used in combination with another active ingredient, such as phentolamine or prazosin, the total amount of the active ingredients may fall within the above amounts. Similarly, when phentolamine or prazosin is used in place of PGE-1 the amount of active ingredient may be within the above amounts.

The penetration of the active ingredient through the skin is enhanced to an acceptable level by including in the composition a skin penetration enhancing effective amount of an enhancer compound which is a 2-substituted 1,3-dioxolane of the formula

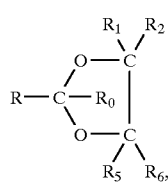

(I)

or a 1,3-dioxane of the formula (II):

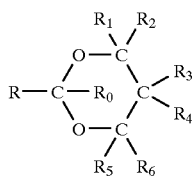

(II)

or an acetal (including hemiacetal) of the formula (III):

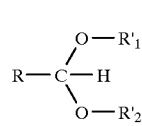

(III)

where R represents a $C_6$ to $C_{20}$ aliphatic group, $R_1$, $R_2$, $R_3$, $R_4$, $R_5$, and $R_6$, each, independently, represent hydrogen or a $C_1$ to $C_4$ aliphatic group.

$R'_1$ and $R'_2$, each, independently, represent $C_1$ to $C_4$ aliphatic group.

Preferably, R represents a $C_6$ to $C_{12}$ aliphatic group; especially $C_7$ to $C_{10}$ aliphatic group. The aliphatic group may be a straight or branched chain alkyl or alkenyl group, such as, for example, n-hexyl, n-heptyl, n-octyl, n-nonyl, n-decyl, n-undecyl, n-dodecyl, n-hexadecyl, n-octadecyl, 2-methyl-octyl, 4-ethyl-decyl, 8-methyl-decyl, n-octenyl, n-stearyl, and the like. The straight chain alkyl groups, such as n-heptyl, n-octyl, n-nonyl and n-decyl, are especially preferred.

The $C_1$ to $C_4$ aliphatic group may be, for example, methyl, ethyl, n-propyl, isopropyl, n-butyl, tert-butyl, ethenyl, and the like. The preferred aliphatic groups for $R_1$ to $R_6$ and for $R'_1$ and $R'_2$ are alkyl groups, especially alkyl having 1 or 2 carbon atoms, most especially ethyl. $R_1$ to $R_6$ may also, preferably, all be hydrogen.

The amount of the enhancer compound will be selected to provide the desired delivery rate for the active compound but, taking into consideration such additional factors as, product stability, side effects, carrier system and the like. Generally, amounts in the range of from about 0.5 to 25%, preferably from about 2 to 15 percent, especially from about 3 to 10 percent, of the composition, will provide stable and effective compositions.

The compositions are generally formulated as gels, especially aqueous-alcoholic gels. However, other forms, such as, for example, lotions, creams, mousses, aerosols, ointments, lubricants, etc., may be used so long as when applied to the genitalia the formulation will stay in place, i.e., without run-off, for sufficient time, to permit an individual to spread the composition over the whole penis, preferably, over only the glans of the penis.

In addition to the above different forms of the composition, the compositions may also be provided for administration by any of the known delivery forms, including, for example, unit dosage and multi-dosage (i.e., multiple unit dosages in a single package or container) forms and bulk forms. As examples of unit dosage forms, mention may be made, for example, of syringes, gelcaps, blister packs, and the like. Bulk forms may be stored in, for example, tubes, bottles, jars, pumps, aerosol containers, and the like, formed of glass, coated metal containers or plastic materials. Again, the formulation and packaging of pharmaceutical products is well within the skill in the art.

It is also within the scope of the invention, and in some cases to enhance stability (e.g., appearance of the composition, such as phase separation; chemical stability of ingredients), to provide the composition in two or more, generally two, parts, with the enhancer compound maintained in a separate container or separate part of the same container, from at least the PGE-1 component. A two part composition, for mixing just prior to use, is especially convenient when the enhancer is an acetal of formula (III) but also for the 1,3-dioxolanes and 1,3-dioxanes. In this regard, under the preferred acidic pH of the composition, e.g., from about 5 to about 6, the acetal, and to lesser extent the dioxolanes and dioxanes, are subject to hydrolysis. Therefore, keeping the enhancer apart from the other ingredients until just prior to use will prevent the hydrolysis of the enhancer compound to proceed to any significant extent, if at all. When supplied in two parts, with the enhancer maintained separately from PGE-1, it is preferred to mix the enhancer with PGE-1 and the other components, prior to application to the genitalia.

Thus, while it is generally most convenient to store the necessary formulation ingredients as a single composition, in this case there is often a practical limitation with respect to storage, or shelf life. That is, the optimum pH for stability of the $PGE_1$ is relatively low, about 5, whereas, the dioxane, dioxolane, or, especially, the acetal, percutaneous penetration enhancers are most stable at a higher pH, usually 6 or greater. Thus, a single formulation will normally compromise the stability of one or both of these components to a greater or lesser degree, depending on the specific pH of the composition. It may, therefore, be more desirable to place the PGE-1 and the enhancer(s) in separate compositions or compartments in the same container, each with its pH optimized for respective stablity, to be mixed immediately before use. Similarly, when the active ingredient includes prazosin the composition should be non-aqueous, i.e., alcohol (ethanol and/or isopropanol) and propylene glycol, or the prazosin should be stored separately from the aqueous media until just prior to use.

Furthermore, the stability of PGE-1 can be affected by its physical form, and, specifically, PGE-1 is generally recognized to be more stable as a solid than in solution. Thus, a two part composition might advantageously, with respect to shelf stability, contain solid, i.e., crystalline, PGE-1 in one part to be dissolved on admixture with fluid ingredients in the second part, to give a single composition ready for immediate use. In this regard, the crystalline PGE-1 may be maintained stably under refrigeration for periods of as long as about 2 years.

However, it is also within the scope of the invention to first apply the enhancer to the genitalia (e.g., the glans penis or the shaft of the penis or the entire penile area, including the scrotum) and then, usually within 30 minutes, preferably within 15 minutes, apply the PGE-1 (together with any other optional drug component) and remainder of the composition.

Moreover, as will be appreciated by those skilled in the art, the pharmaceutically acceptable carrier may be present, in whole, or in part, with either or both of the enhancer and PGE-1, taking into consideration such factors as solubilities, product stability, ease of application, and the like.

In this regard, PGE-1 is hardly soluble in water but quite soluble in ethanol. Moreover, this solubility is not impaired to a practical degree by the incorporation of the water-insoluble enhancer compound used in this invention.

Accordingly, the carrier system for the PGE-1 and enhancer components is preferably an aqueous or non-aqueous alcoholic carrier containing sufficient alcohol, especially ethanol and/or isopropanol, to solubilize the essentially water-insoluble PGE-1, and be miscible with the enhancer. Generally, however, depending on the amounts of enhancer and PGE-1 in the formulations the aqueous alcoholic carrier can contain from about 10% to about 90% of ethyl alcohol or isopropyl alcohol, preferably, from about 60 to about 80 percent of ethanol or from about 45 to 55 percent of isopropanol. Mixtures of ethanol and isopropanol in proportions providing the desired solubility of PGE-1 and compatibility with the enhancer can also be used.

Again, the total amount of the aqueous or non-aqueous, alcoholic carrier will depend on the amount of PGE-1, other active ingredient, amount and type of enhancer, and the form of the composition, e.g., gel, cream, ointment, etc. Usually amounts of the aqueous or non-aqueous alcoholic carrier within the range of from about 70% to about 97% may be used.

In the preferred compositions which are in the form of a gel, a thickening agent, such as hydroxypropyl cellulose, will be included as a gelling agent. However, any other pharmaceutically acceptable thickening/gelling agent may be used. For example, mention may be made of other cellulosic ethers, polymeric thickening agents, e.g., acrylic acid polymers, Carbopol® thickeners, etc., xanthan gum, guar gum, and the like, as well as inorganic thickeners/gelling agents. The amount of the thickening agent is not particularly critical and can be selected to provide the desired product consistency or viscosity to allow for easy application to the genitalia but which will not be too watery or loose so that it will stay where applied. In this regard, it may often be advantageous for the composition to be applied to the genitalia while the person is standing. Generally, depending on its molecular weight, amounts of thickening agent up to about 5%, such as, for example, from 0.1 to about 2%, of the composition will provide the desired effect.

While the compositions of this invention generally have little or no side affects, especially penile pain, a percentage of individuals in the general population may experience some minor discomfort, such as a burning sensation, especially when applied to the shaft of the penis. When applied to the glans of the penis the tendency for a burning sensation is further lessened. This is another advantage of the present invention, namely, that the compositions are more effective when applied to only the glans of the penis. As noted above, the effectiveness of the composition when applied to only the glans (a non-cornified tissue) was not at all expected in view of the evident mode of action of the enhancers, such as, dioxolane, dioxane and acetal enhancers.

In any case, especially when it is intended to apply the composition to the entire penis and/or genital area, it is also within the scope of the invention to include in the compositions a minor amount, for example, up to about 5%, especially up to about 3%, such as from about 0.1 to 1 or 2%, of a mild local anesthetic or anti-burning or anti-itching agent. While many such agents are known in the art, satisfactory results have been achieved with menthol. Other mild local anethestics, such as, for example, chlorobutanol, camphor, benzyl alcohol, etc., may be used.

For treatment of erectile dysfunction and with the preferred application on the glans penis, the amount of formulation to be applied is preferably in the range of from about 0.1 to about 1 milliliter (ml), preferably, from about 0.1 to 0.5 ml, more preferably from about 0.2 to 0.3 ml. For these preferred application rates the active ingredient will be contained in the formulation in the amounts as described above, namely, from about 0.001 to 5.0%, preferably 0.05 to 1.5%, more preferably 0.05 to 1.0%.

For a typical, representative gel formulation according to the invention containing 0.5% of PGE-1 and 5% of 2-n-nonyl-1,3-dioxolane, suitable dosage amounts, as a function of the intended use and area of application, may be from about 0.1 to about 0.5 ml, preferably from about 0.2 to 0.3 ml, such as, for example, 0.25 ml.

Representative alcohol gel (non-aqueous) and aqueous alcoholic gel formulations according to the invention are shown below, with the amounts for "broad", "intermediate" and "preferred" ranges being parts by weight.

|  | Broad | Intermediate | Preferred |
|---|---|---|---|
| Ethanol or Isopropanol Gel | | | |
| PGE-1 | 0.001–5.0 | 0.05–1.5 | 0.05–1.0 |
| Enhancer | 0.5–25 | 2–15 | 3–12 |
| Carrier: | 50–98 | 70–97 | 80–94 |
| Ethanol/Water (or) | 45/55–90/10 | 50/50–90/10 | 55/45–90/10 |
| i-Propanol/Water | 30/70–90/10 | 35/65–90/10 | 40/60–90/10 |
| Gelling Agent | 0.1–5.0 | 0.2–2.0 | 0.4–1.2 |
| Ethanol or Isopropanol Gel with Menthol | | | |
| PGE-1 | 0.001–5.0 | 0.05–1.5 | 0.05–1.0 |
| Enhancer | 0.5–25 | 2–15 | 3–12 |
| Carrier: | 50–98 | 70–97 | 80–94 |
| Ethanol/Water or | 45/55–90/10 | 50/50–90/10 | 55/45–90/10 |
| i-Propanol/Water | 30/70–90/10 | 35/65–90/10 | 40/60–90/10 |
| Gelling Agent | 0.1–5.0 | 0.2–2.0 | 0.4–1.2 |
| Menthol | 0.1–5.0 | 0.2–3.0 | 0.2–1.0 |
| Propylene Glycol/Alcohol Gel | | | |
| PGE-1 | 0.05–5.0 | 0.05–1.5 | 0.05–1.0 |
| Enhancer | 0.5–25 | 2–15 | 3–12 |

-continued

|  | Broad | Intermediate | Preferred |
|---|---|---|---|
| Carrier: | 50–98 | 70–97 | 80–94 |
| C2/C4 Alkanol | 10–90 | 20–70 | 40–50 |
| Propylene Glycol | 2–80 | 5–60 | 10–50 |
| Water | 0–45 | 0–40 | 0–40 |
| Gelling Agent | 0.1–5.0 | 0.2–2.0 | 0.4–1.2 |
| Menthol | 0–5.0 | 0–3.0 | 0–1.0 |

Although it is difficult to measure pH of the compositions, the compositions tend to be mildly acidic, due to the acidic nature of PGE-1. Generally, pH modifying agents (e.g., acids or bases) are not preferred in the invention compositions.

It is a particular advantage of the preferred compositions of this invention that they remain stable against phase separation and product degradation over a wide range of storage conditions. For example, the aqueous and non-aqueous alcoholic gel formulations as described above remain stable over a temperature range of at least from about −18° C. to about 10° C., over periods of several months to years, depending on the storage temperature. The lower the temperature, the greater the stability. Within this temperature range the concentration of PGE-1 remains at over 80% of the original concentration. At lower temperatures which might, in some cases, cause phase separation of the PGE-1, the composition may be restored to its original condition upon thawing. Accordingly, it is often preferred that the compositions be refrigerated until just prior to use.

Another particular advantage of the present invention is that by virtue of the enhancement of the effectiveness of PGE-1 it is possible to use less of the active ingredient, thereby lessening the likelihood of irritation or other side effects.

Although the compositions of the invention are effective without any additional assistance a better erection, i.e., more suitable for intercourse, especially when the composition is applied directly and only to the glans, may sometimes be achieved by combining the topical transdermal application of the active ingredient, as described above, with the assistance of a mechanical vienous constrictor, such as a rubber band or other "strangulation" device. Such devices are well known in the art. In the contest of the present invention it is believed that the assistance of a mechanical constriction device, preferably applied at or near the base of the shaft of the penis, may enhance the effectiveness of the active ingredient by more effectively directing the active ingredient to enter the corpus cavernosum.

REFERENTIAL EXAMPLE 1

The following aqueous alcoholic gel according to the invention was prepared:

|  | Amount (percent) |
|---|---|
| Prostaglandin $E_1$ | 0.1 |
| 2-n-nonyl-1,3-dioxolane | 5.0 |
| Hydroxypropyl cellulose (HPC) | 1.0 |
| Solvent (Ethanol/Water: 70/30) | q.v. 100 |

The 2-n-nonyl-1,3-dioxolane is added to the ethanol/water solvent while stirring to form a clear solution. Solid (crystalline) PGE-1 (commercially available from a number of different sources) is added, under stirring, and allowed to dissolve. The HPC (powder) is added next with continued mixing until uniform gelation is observed.

The mixing is carried out under ambient temperature but can be carried out at colder temperature if desired. Also, mixing can, if desired, be carried out using a roller mill for mixing the ingredients under reduced shear conditions.

REFERENTIAL EXAMPLE 2

The following aqueous alcoholic gel according to the invention was prepared:

|  | Amount (percent) |
|---|---|
| Prostaglandin $E_1$ | 0.5 |
| 2-n-nonyl-1,3-dioxolane | 5.0 |
| Hydroxypropyl cellulose (HPC) | 1.0 |
| Solvent (Ethanol/Water: 70/30) | q.v. 100 |

REFERENTIAL EXAMPLE 3

The following aqueous alcoholic gel according to the invention was prepared:

|  | Amount (percent) |
|---|---|
| Prostaglandin $E_1$ | 0.5 |
| 2-n-nonyl-1,3-dioxolane | 5.0 |
| Hydroxypropyl cellulose (HPC) | 1.0 |
| Menthol | 0.5 |
| Solvent (Ethanol/Water: 70/30) | q.v. 100 |

REFERENTIAL EXAMPLE 4

The following aqueous alcoholic gel according to the invention was prepared:

|  | Amount (percent) |
|---|---|
| Prostaglandin $E_1$ | 0.1 |
| 2-n-nonyl-1,3-dioxolane | 5.0 |
| Hydroxypropyl cellulose (HPC) | 1.0 |
| Menthol | 0.5 |
| Solvent (Ethanol/Water: 50/50) | q.v. 100 |

REFERENTIAL EXAMPLE 5

The following aqueous alcoholic gel according to the invention was prepared:

|  | Amount (percent) |
|---|---|
| Prostaglandin $E_1$ | 0.5 |
| 2-n-nonyl-1,3-dioxolane | 5.0 |
| Hydroxypropyl cellulose (HPC) | 1.0 |
| Menthol | 0.5 |
| Solvent (Ethanol/Water: 50/50) | q.v. 100 |

EXAMPLE 1 a) A 57 year old subject applied to the glans of the penis 0.25 ml of the gel described in Referential Example 4. Tumescence was experienced within 30 minutes.

b) On another occasion, this same subject applied to the glans of the penis 0.25 ml of the gel described in Referential Example 2. Tumescence was experienced within 20 minutes. A full, unstimulated erection was experienced within 30 minutes and lasted for about one hour.

c) On another occasion, this subject applied to the glans of the penis 0.25 ml of the gel described in Referential Example 3. Tumescence was experienced within 30 minutes. Upon visual stimulation at 45 minutes after application, a full erection was experienced.

d) On two different occasions, this subject applied to the glans of the penis 0.25 ml of the placebo gel, i.e. devoid of Prostaglandin $E_1$. No tumescence or erection was experienced on either occassion, even upon visual stimulation.

EXAMPLE 2

A 44 year old male applied to the glans of the penis 0.25 ml of the gel described in Referential Example 2. This individual felt that the blood flow, or enlargement, of the penis was greater than normally experienced during intercourse.

EXAMPLE 3 a) A 47 year old male applied to the glans of the penis 0.5 ml of the gel described in Referential Example 4. The subject reported a pleasant feeling of always having a partial erection hours after use—even after washing the gel off the skin surface.

b) on an other occasion, th is subject applied to the glans of the penis 0.25 ml of the gel described in Referential Example 5, with similar positive results.

EXAMPLE 4

The formula of Reference Examples 1 was studied in placebo controlled clinical trials involving 34 impotent individuals. The placebo was the formulation described in Referential Examples 1 and 2 but devoid of Prostaglandin $E_1$. The formulation was tested by applying volumes that contained 0.5 mg (Dose A) or 1.0 mg (Dose B) of PGE-1 to the penis. Erections were observed for 8 to 12 (67%) men treated with Dose A and for 7 out of 10 (70%) men treated with Dose B, while only 2 of 12 men experienced erections when treated with the placebo gel.

What is claimed is:

1. A stable aqueous alcoholic composition for topical administration to the penis of a person in need thereof, said composition comprising
   (a) a pharmacologically effective amount of prostaglandin $E_1$;
   (b) a penetration enhancing effective amount of a skin penetration enhancing compound selected from the group consisting of $C_6$ to $C_{20}$-hydrocarbyl group substituted 1,3-dioxane, 1,3-dioxolane and acetal; and
   (c) a pharmaceutically effective carrier to solubilize components (a) and (b) and comprising
      (i) a mixture of ethyl alcohol and water effective to solubilize the components (a) and (b); or
      (ii) a mixture of isopropyl alcohol and water effective to solubilize the components (a) and (b); or
      (iii) a mixture of ethyl alcohol, isopropyl alcohol and water.

2. The composition of claim 1 comprising
   (a) from about 0.01 to about 5 percent by weight of prostaglandin $E_1$;
   (b) from about 0.5 to about 15 percent by weight of said skin penetration enhancing compound;
   (c) (i) a mixture of ethyl alcohol and water at a mixing ratio, by weight, of about 90:10 to about 45:55; or
      (ii) a mixture of isopropyl alcohol and water at a mixing ratio, by weight, of about 90:10 to about 30:70;
   and further comprising
   (d) up to about 5 percent by weight of thickening agent; and
   (e) up to about 5 percent by weight of menthol.

3. The composition of claim 1 comprising
   (a) from about 0.05 to about 2 percent by weight of prostaglandin $E_1$;
   (b) from about 2 to about 15 percent by weight of said skin penetration enhancing compound;
   (c) (i) a mixture of ethyl alcohol and water at a mixing ratio, by weight, of about 50:50 to about 90:10, or
      (ii) a mixture of isopropyl alcohol and water at a mixing ratio, by weight, of about 35:65 to about 90:10;
   (d) up to about 2 percent by weight of thickening agent; and
   (e) from 0 to about 2 percent by weight of menthol.

4. The composition of claim 3 comprising
   (a) from about 0.05 to about 1 percent by weight of prostaglandin $E_1$;
   (b) from about 3 to 12 percent by weight of said skin penetration enhancing compound;
   (c) from about 70 to about 97 percent by weight of the pharmaceutically effective carrier;
   (d) from about 0.2 to about 2 percent by weight of thickening agent; and
   (e) from 0 to about 2 percent by weight of menthol.

5. The composition of claim 4 wherein menthol is present.

6. The composition of claim 1 wherein component (b) comprises from about 2 to about 15 percent by weight of $C_7$ to $C_{12}$-alkyl substituted 1,3-dioxolane.

7. The composition of claim 1 wherein component (b) comprises from about 2 to about 15 percent by weight of $C_7$ to $C_{12}$-alkyl substituted acetal.

8. The composition of claim 1 wherein the composition has a pH in the range of from about 5 to about 6.

9. A composition for topical administration to the penis of a person in need thereof, said composition comprising
   (a) a pharmacologically effective amount of a mixture of prostaglandin $E_1$ with phentolamine or prazosin;
   (b) a penetration enhancing effective amount of a skin penetration enhancing compound selected from the group consisting of $C_6$ to $C_{20}$-hydrocarbyl group substituted 1,3-dioxane, 1,3-dioxolane and acetal; and
   (c) a pharmaceutically effective carrier effective to solubilize components (a) and (b) and comprising
      (i) a mixture of ethyl alcohol and water effective to solubilize the components (a) and (b); or
      (ii) a mixture of isopropyl alcohol and water effective to solubilize the components (a) and (b); or
      (iii) a mixture of ethyl alcohol, isopropyl alcohol and water.

10. A method for treating penile erectile dysfunction in a person in need thereof comprising topically administering to the genitalia of the patient a composition comprising a pharmacologically effective amount of prostaglandin $E_1$ or a mixture of prostaglandin $E_1$ with phentolamine or prazosin, in the presence of a skin penetration enhancing effective amount of a skin penetration enhancing compound selected from the group consisting of $C_6$ to $C_{20}$-hydrocarbyl group substituted 1,3-dioxolane, 1,3-dioxane and acetal; wherein the active ingredient and the skin penetration enhancing compound are solubilized in a pharmacologically acceptable aqueous alcoholic carrier comprising ethyl alcohol and water or isopropyl alcohol and water, or a mixture of ethyl alcohol, isotropyl alcohol and water which retain the active ingredient and skin penetration enhancing compound on the genitalia to allow the active ingredient to be absorbed.

11. The method of claim 10 which further comprises an anti-irritating effective amount of menthol in said composition.

12. The method of claim 10 which comprises topically administering said composition to only the glans of the penis.

13. The method of claim 12 which further comprises applying mechanical venous constriction to the shaft of the penis.

14. The method of claim 10 which further comprises applying mechanical venous constriction to the shaft of the penis.

15. The method of claim 10 which comprises topically administering said composition to provide from about 25 µg to about 4 mg of prostaglandin $E_1$ to the glans of the penis.

16. The method of claim 10 which comprises topically administering said composition to provide from about 50 µg to about 2.5 mg of prostaglandin $E_1$ to the glans of the penis.

17. The composition according to claim 4 wherein the amount of prostaglandin $E_1$ is in the range of about 0.1 to about 1 percent by weight and the skin penetration enhancing compound comprises 2-n-nonyl-1,3-dioxolane in an amount of from about 3% to about 12% by weight.

18. The composition according to claim 17 having a pH of from about 5 to about 6.

19. The composition according to claim 4 wherein the amount of prostaglandin $E_1$ is about 0.5% to about 1% by weight and the amount of 2-n-nonyl-1,3-dioxolane is about 5% by weight.

20. The composition according to claim 19 having a pH of from about 5 to about 6.

21. The method of claim 16 which comprises topically administering said composition containing about 3% to about 12% by weight of the composition of 2-n-nonyl-1,3-dioxolane.

22. The method of claim 16 which comprises topically administering said composition containing from about 5% to about 10% by weight of the composition of 2-n-nonyl-1,3-dioxolane.

23. The method of claim 16 which comprises topically administering said composition containing about 5% by weight of the composition of 2-n-nonyl-1,3-dioxolane.

\* \* \* \* \*